United States Patent [19]

Fond

[11] Patent Number: 5,111,683
[45] Date of Patent: May 12, 1992

[54] CALIBRATION METHOD FOR A PULSE RESPONSE FLOWMETER

[75] Inventor: Andre Fond, Meyzieu, France

[73] Assignee: HOSPAL Industrie, Meyzieu, France

[21] Appl. No.: 566,499

[22] Filed: Aug. 13, 1990

[30] Foreign Application Priority Data

Aug. 16, 1989 [FR] France .................. 89 11083

[51] Int. Cl.⁵ .................................. G01F 25/00
[52] U.S. Cl. ............................. 73/3; 364/571.02
[58] Field of Search ..... 73/3; 364/510, 571.01–571.08

[56] References Cited

U.S. PATENT DOCUMENTS

| 3,092,991 | 6/1963 | Thompson, Jr. .................. 73/3 |
| 3,517,308 | 6/1970 | Mirdadian ....................... 73/3 X |
| 4,192,184 | 3/1980 | Cox et al. ...................... 73/32 A X |
| 4,419,898 | 12/1983 | Zanker et al. .................. 73/3 X |
| 4,437,340 | 3/1984 | Csere et al. .................... 73/3 X |
| 4,528,857 | 7/1985 | Bruner .......................... 73/861.18 |
| 4,638,233 | 1/1987 | Erdman ......................... 73/3 X |
| 4,754,641 | 7/1988 | Orban et al. .................... 73/3 X |
| 4,848,897 | 7/1989 | Aizu et al. ..................... 128/691 X |
| 4,906,165 | 3/1990 | Fox et al. ...................... 417/12 |
| 4,977,528 | 12/1990 | Norris ........................... 73/3 X |

FOREIGN PATENT DOCUMENTS

| 298857 | 1/1989 | European Pat. Off. .......... 73/3 |
| 11765 | 1/1979 | Japan ............................ 73/3 |
| 269019 | 11/1986 | Japan ............................ 73/3 |
| 2195448 | 4/1988 | United Kingdom ............. 73/3 |

Primary Examiner—Tom Noland
Attorney, Agent, or Firm—Finnegan, Henderson, Farabow, Garrett & Dunner

[57] ABSTRACT

The invention relates to a method of and apparatus for calibrating flowmeters which may be employed in a dialysis liquid circuit. The invention includes the steps of measuring during a data acquisition stage of a specified duration (Ta), each elementary period ($T_7(i)$, $T_8(i)$) separating two pulses staggered by a specified time measurement span (P), counting the number of pulses (n, m) emitted during the acquisition stage (Ta), and calculating the mean calibration period.

17 Claims, 5 Drawing Sheets

CALIBRATION METHOD FOR A PULSE RESPONSE FLOWMETER

BACKGROUND OF THE INVENTION

1. Field of the Invention

The present invention concerns the general technical field of the metering of the flow of a fluid circulating in a circuit by means of a pulse response flowmeter and it concerns, more precisely, the calibration of such flowmeters.

2. Description of the Relate Art

The invention is particularly advantageous in metering the flow of a dialysis liquid circulating in a haemodialyser of an artificial kidney.

In the above mentioned preferred application, an artificial kidney comprises in the conventional way a haemodialyser with two compartments separated by a membrane, one compartment being connected to the circuit of the dialysis liquid, and the other compartment being connected to a patient via an extracorporeal blood circuit. The circuit of the dialysis liquid is provided upstream and downstream of the haemodialyser, with flowering generating an electric pulse as a specified fraction of liquid passes.

During a dialysis session, the excess liquid present in the blood is subjected to ultrafiltration through a membrane because of the pressure gradient on either side of the membrane. Before such a session one proceeds with a stage of calibrating the flowmeters for which the haemodialyser is bypassed and an identical flow of dialysis liquid circulates in the two flowmeters. This calibration stage includes metering the calibration frequencies of each flowmeter by counting the number of pulses during a chosen period, to define the relation existing between a metering frequency and a given rate of flow of the dialysis liquid. Such a calibration stage permits a partial correction of the intrinsic errors of the flowmeters, and also permits the use flowmeters of different types.

The calibration of the flowmeters deriving from experimental measurements is vitiated by a certain error systematically affecting the results of the subsequent measurements. It is therefore indispensable to reduce as far as possible the accidental metering errors liable to occur during the calibration stage, to obtain a maximum metering accuracy for determining the ultrafiltrate removed from the patient's blood.

To attempt to reduce the importance of the metering errors, such as artifacts, the prior art generally proposes to proceed with a calibration step of a rather long duration.

Moreover, the patent application EP A 88 304 162.6 (publication no. 0 298 587 A2) proposes a method tending to limit the errors in flow measurements, in particular during a calibration stage of the flowmeters equipping a haemodialyser. This document proposes to mount in series in the dialysis liquid circuit a pair of flowmeters upstream of the haemodialyser and another pair downstream of the haemodialyser. During the calibration stage, the maemodialyser is bypasses so that the four flowmeters are placed in series. The frequencies of the flowmeters are measured and the calibration is considered to be valid if the deviations between the measured frequencies fall within a specified range of values.

The main drawback of the method described above lies in the fact that the accuracy of the metering depends directly on the acquisition period during which the pulses are counted. Thus in order to reach a high accuracy, it is necessary to increase the time during which the measurements are acquired to a prohibitive extent.

Moreover, it has proved in practice, that the flowmeters show a metering disparity during a dialysis session generally lasting four hours. It then becomes necessary to proceed with calibrations during the dialysis session to eliminate this error, which reduces the dialysis efficiency because of the long duration of the calibration stage.

Moreover, the doubling of the flowmeters increases the operating cost of such a method.

SUMMARY OF THE INVENTION

Thus the object of the present invention is to remedy the drawbacks set forth above by providing a calibration method for a flowmeter delivering an electric pulse signal allowing a high metering accuracy to be obtained irrespective of the calibration period.

Another object of the invention is to offer a method allowing the calibration of the flowmeters to be obtained over a very short period, while ensuring the elimination of accidental metering errors, such as artifacts or interference.

Another object of the invention is to propose a method particularly suitable for the calibration of rotary pulse response flowmeters.

A further object of the invention is to provide a method suitable for ensuring the calibration of flowmeters equipping more particularly a dialysis liquid circuit of an artificial kidney.

To attain the objects set out above, the calibration method in accordance with the invention includes:
 measuring during a data acquisition stage of a specified duration each elementary period separating two pulses staggered by a specified measurement span.
 counting the number of pulses emitted during the acquisition stage,
 and, calculating the mean calibration period.

Thanks to this method, one eliminates the inaccuracy linked, in the known calibration methods, to taking into account the space of time corresponding to the shift between the start (end) of the data acquisition stage and the first (last) pulse counted in the calibration duration properly so called, (which strictly speaking, should extend over an integral number of pulses). Moreover, this method allows the collected data to be subsequently processed, making it possible in particular, to minimize the importance of erratic data or to eliminate them.

In a preferred mode of embodiment, wherein each flowmeter is of the rotary type with N pulses generated per rotor turn, the calibration method lies, in determining the mean calibration period:
 in calculating the successive rotation periods, by proceeding for each one of them to the summation of N consecutive elementary periods, these successive rotation periods being advantageously chosen so as to overlap over at least one elementary period;
 and in processing the rotation period, to determine the mean calibration period.

Thanks to this mode of embodiment, it is possible, on the one hand, to become independent of the possible scatter in the values of the acquired data due to the mechanical or geometrical characteristics of the flowmeter (it being possible for this scatter to become an impediment when it is intended to subject these data to subsequent statistical processing), and on the other hand, to have available a sufficient number of data for effecting a very accurate calibration in a very short space of time.

The object of the invention is also to provide a control and processing device suitable for the calibration of flowmeters comprising:
- a microprocessor connected to two flowmeters via a link line,
- a counter capable of measuring each elementary period separating two pulses emitted by each one of the flowmeters,
- a means for counting the pulses emitted during the elementary periods considered,
- and programming means for processing the elementary periods in order to determine a mean calibration period for each flowmeter.

Various other characteristics will emerge from the description given below with reference to the attached drawings showing modes of embodiment of the object of the invention by way of nonrestrictive examples.

DESCRIPTION OF THE PREFERRED EMBODIMENTS

The method in accordance with the invention is intended to ensure the calibration of at least one flowmeter equipping a circulation circuit of a given fluid, so as to obtain a high measurement accuracy of the order of 5/10,000. Such a method is particularly suitable for the calibration of flowmeters of the type each delivering an electric pulse whose frequency corresponds to a given value of the flow of the fluid.

Advantageously, the flowmeters calibrated according to the method in accordance with the invention may equip a circuit of a dialysis liquid of an artificial kidney. In the example illustrated in FIG. 1, the artificial kidney comprises a circuit 1 of a dialysis liquid connected to the first compartment 2 of a haemodialyser 3. In the conventional way, the haemodialyser 3 comprises a second compartment 4 separated from the first, by a membrane 5 and connected to the patient via an extracorporeal blood circuit 6.

Figure 1:
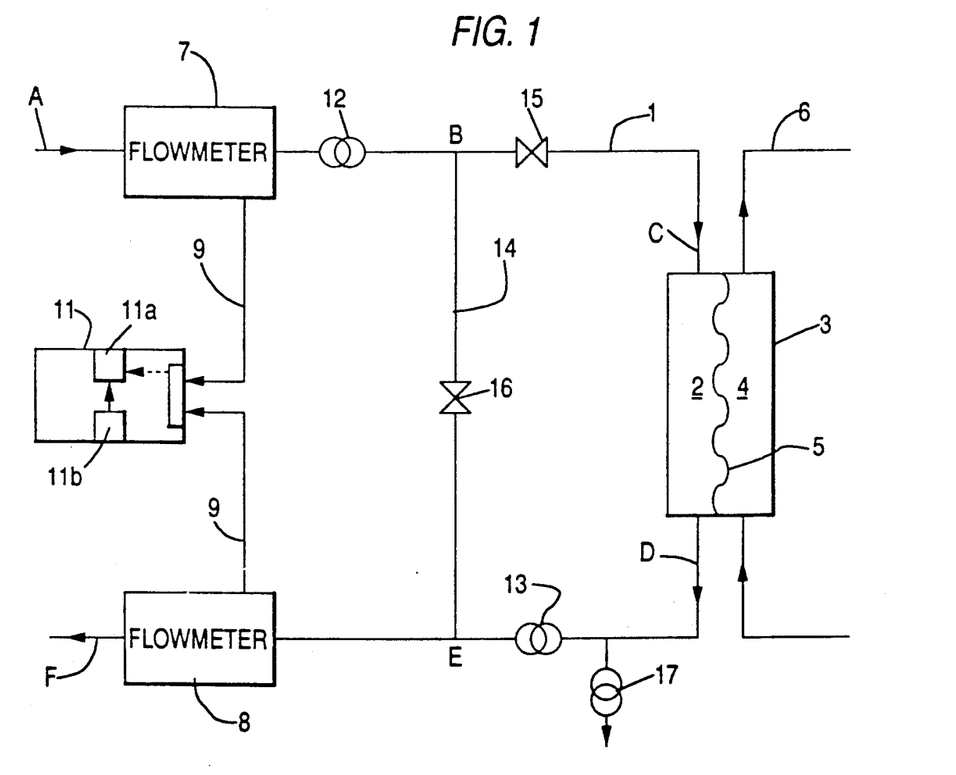
FIG. 1 shows a diagram of a mode of embodiment of an artificial kidney provided with flowmeters adapted for calibration according to the method in accordance with the invention.

The circuit 1 comprises an intake A connected to a source of the dialysis liquid (not shown), as well as an outlet F connected to evacuation or recycling means, not shown. The dialysis circuit 1 is provided with flowmeters 7 and 8 respectively up the line and down the line from the haemodialyser ensuring the metering of the quantity of circulating liquid, by each flowmeter generating an electric pulse after the passing of a specified fraction of dialysis liquid. Preferably, but not exclusively, the flowmeters 7 and 8 are of an identical kind and of the rotary type. Each flowmeter delivers a number N of electric pulses per turn of the rotor. Each pulse is emitted on passing a gradation or mark carried by the rotor or, for example, a blade passing in front of a fixed detector. Such an electric signal is transmitted via a line 9 to a control and processing device 11 whose function will emerge more clearly in the remaining part of the description.

The circuit 1 also comprise circulating pumps 12, 13 placed, for example, respectively between the flowmeter 7 up the line and the intake C of the haemodialyser, and between the outlet D of the haemodialyser and the flowmeter 8 down the line. The circuit 1 is also provided with a bypass line 14, connected on the one hand, at a point B of the circuit to the intake C of the haemodialyser via an obturation means 15, such as a stop valve, and, on the other hand, at a point E of the circuit, to the outlet D of the haemodialyser via the circulating pump 13. The function of the bypass line 14 provided with an obturation means 16 will become clear in greater detail when the calibration stage is discussed.

To proceed to the calibration stage of each one of the two flowmeters, the haemodialyser 3 is bypassed by closing the stop valve 15 and opening the obturation means 16, while the circulating pump 13 is in the stop position. Thus the dialysis liquid is circulating by means of the pump 12 in the circuit formed by the sections A, B, E, F. During this calibration stage, the liquid flow circulating in the flowmeter 7 up the line is exactly the same as the flow of liquid circulating in the flowmeter 8 down the line, inasmuch as the circuit thus formed does not have any point of loss or gain of the dialysis liquid.

Figure 2:
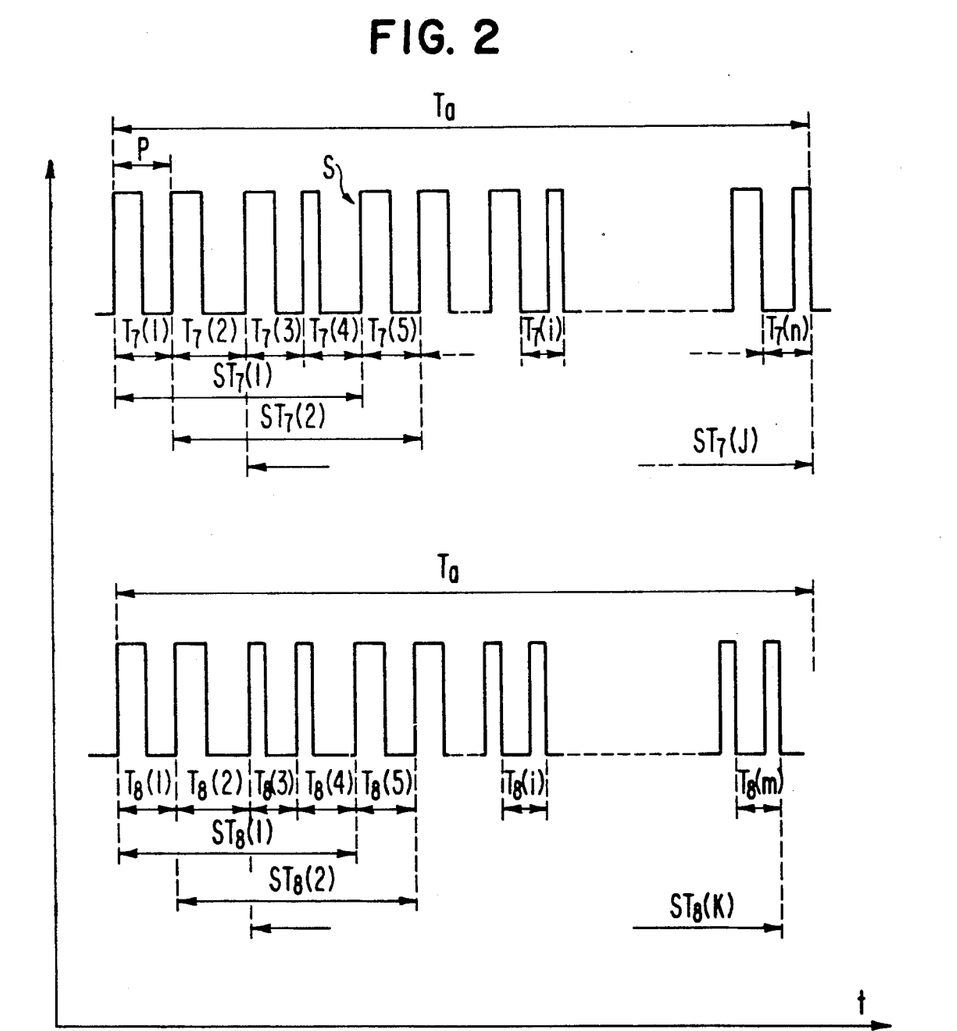
FIG. 2 shows chronograms illustrating the calibration method in accordance with the invention.
Figure 3:
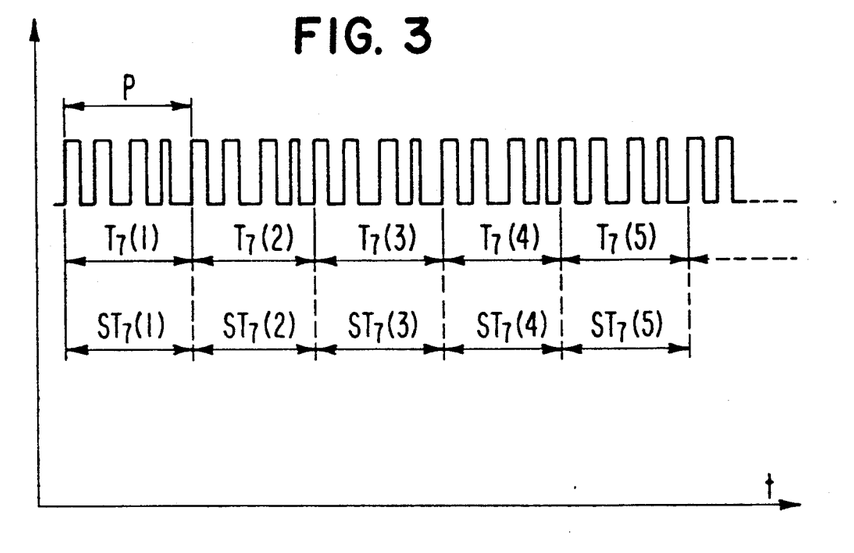
FIG. 3 represents chronograms illustrating a characteristic detail of the calibration method in accordance with the invention.

As seen more precisely in FIG. 2, the calibration method in accordance with the invention lies in measuring, during a data acquisition stage of a chosen duration Ta, to measure for each flowmeter 7, 8, each elementary period $T_7(i)$ and $T_8(i)$ separating two pulses s interspaced by a specified measurement span P. Each pulse is defined as being the part of the signal separating for example, two successive rising fronts. In the example illustrated in FIG. 2, the measurement span P is equal to 1, so that each measured elementary period corresponds to the duration of one pulse. With high frequencies such as illustrated in FIG. 3, the measurement span P is 4, so that each elementary period corresponds to the duration of four pulses.

It should be considered that the duration Ta constitutes in reality a mean data acquisition time. Indeed, such an acquisition stage is intended to allow the registering of an integral and maximum number of elementary periods whose sum does not correspond exactly and necessarily to the duration Ta, as is clearly shown in FIG. 2.

The method also lies in counting for each flow meter 7, 8 the number of respective pulses n and m emitted during the acquisition time Ta and in then calculating the mean calibration periods Tm.

According to a first variant of the embodiment, each mean calibration period $Tm_7$, $Tm_8$, is calculated by establishing the sum of the elementary periods over the number of pulses counted, i.e.:

$$Tm_7 = \frac{1}{n} \cdot \sum_{i=1}^{n} T_7(i)$$

and $$Tm_8 = \frac{1}{m} \cdot \sum_{i=1}^{m} T_8(i)$$

Figure 4:
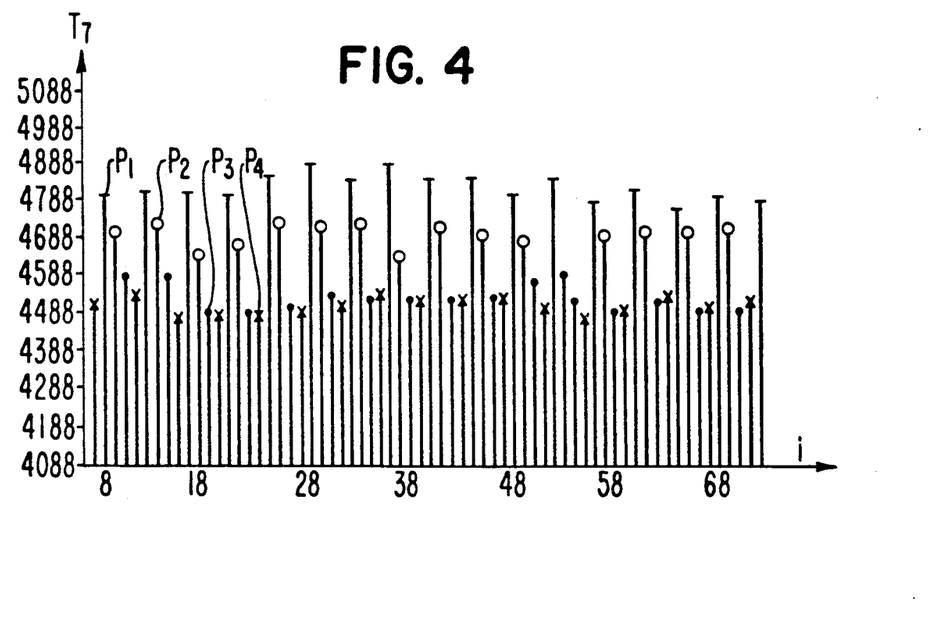
FIG. 4 is a diagram showing the scatter of the measurements taken according to the method of the invention for a rotary flowmeter.

According to a second preferred variant of the embodiment, wherein each flowmeter is of the rotary type with N pulses generated per turn of the rotor, the mean calibration periods are determined by taking into account the scatter in the mechanical characteristics of such flowmeters. Indeed, according to this variant, each elementary period measured between two successive pulses corresponds to the time interval separating the passing of two successive marks or blades in front of the detector. It must also be considered that the elementary periods are not identical inasmuch as the N blades or marks are not regularly interspaced angularly over the rotor. Such a phenomenon appears clearly in FIG. 4 showing a diagram representing by way of example the differences in values between the elementary periods $T_7$ according to the considered rank of the blades of a flowmeter. In the example illustrated, the flowmeter comprises four blades $P_1$ to $P_4$.

The calibration method in accordance with the invention aims to overcome such a shift in the angular implantation to allow the most accurate calibration period possible to be determined. For this purpose, the method in accordance with the invention makes provision for calculating for each flowmeter a series of successive periods of rotation $ST_7(i)$ and $ST_8(i)$.

As shown more precisely in FIG. 2, these rotation periods are determined by proceeding, for each one of them, to the sum of N consecutive elementary periods and by shifting one elementary period at each successive period of rotation, so as to eliminate from the sum the first elementary period of the preceding period, and to add to the sum the elementary period following the last elementary period that was taken into account for the preceding period. In other words, two consecutive rotation periods $ST_7(i)$, $ST_7(i+1)$ (respectively $ST_8(i)$, $ST_8(i+1)$) overlap over (N−1) elementary periods. Provision may also be made for two consecutive rotation periods to overlap over a smaller number of elementary periods.

By way of example, if the number N of blades is equal to four, each rotation period $ST_7(i)$ or $ST_8(i)$ is equal to the sum of the four elementary periods. Thus the first rotation periods $ST_7(1)$ and $ST_8(1)$ are such that $$ST_7(1) = T_7(1) + T_7(2) + T_7(3) + T_7(4)$$

$$ST_8(1) = T_8(1) + T_8(2) + T_8(3) + T_8(4)$$

The second rotation periods are calculated by eliminating the first elementary period from the sum and by taking into account the fifth elementary period, so that:

$$ST_7(2) = T_7(2) + T_7(3) + T_7(4) + T_7(5)$$

and $$ST_8(2) = T_8(2) + T_8(3) + T_8(4) + T_8(5)$$

The following rotation periods are obtained by establishing an identical shift up to the final measured elementary period $ST_7(J)$ and $ST_3(K)$. The number J, K of the rotation periods of the flowmeters 7, 8 respectively is such that:

$$J = n \cdot (N-1)$$

$$K = m \cdot (N-1)$$

Such a method thus permits the elimination of the effect of the asymmetrical angular implantation of the blades, or of the marks on the rotor, by taking into account the rotation period corresponding to one turn of rotation of the rotor of a flowmeter.

Figure 5A:
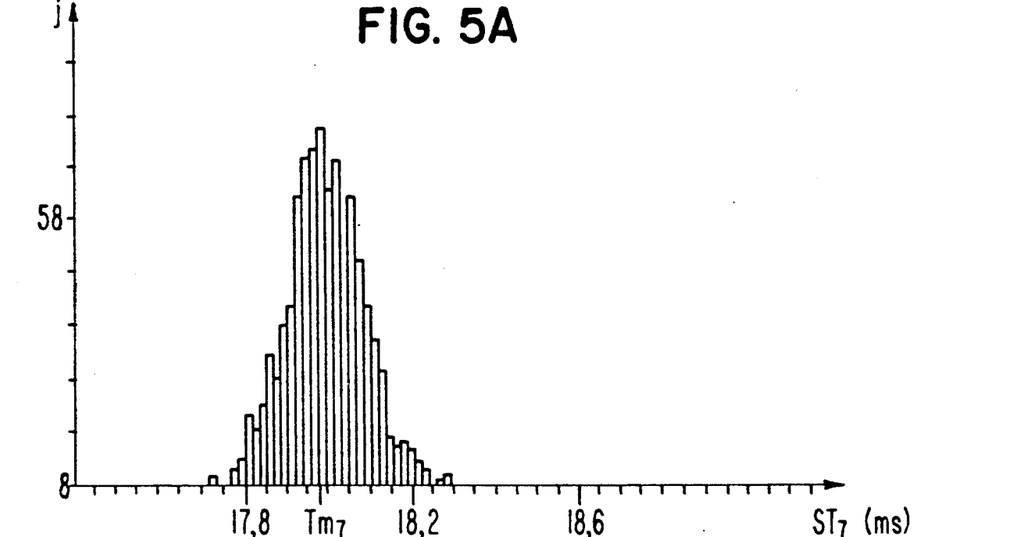
FIGS. 5A and 5B are histograms showing another characteristic detail of the method in accordance with the invention.
Figure 5B:
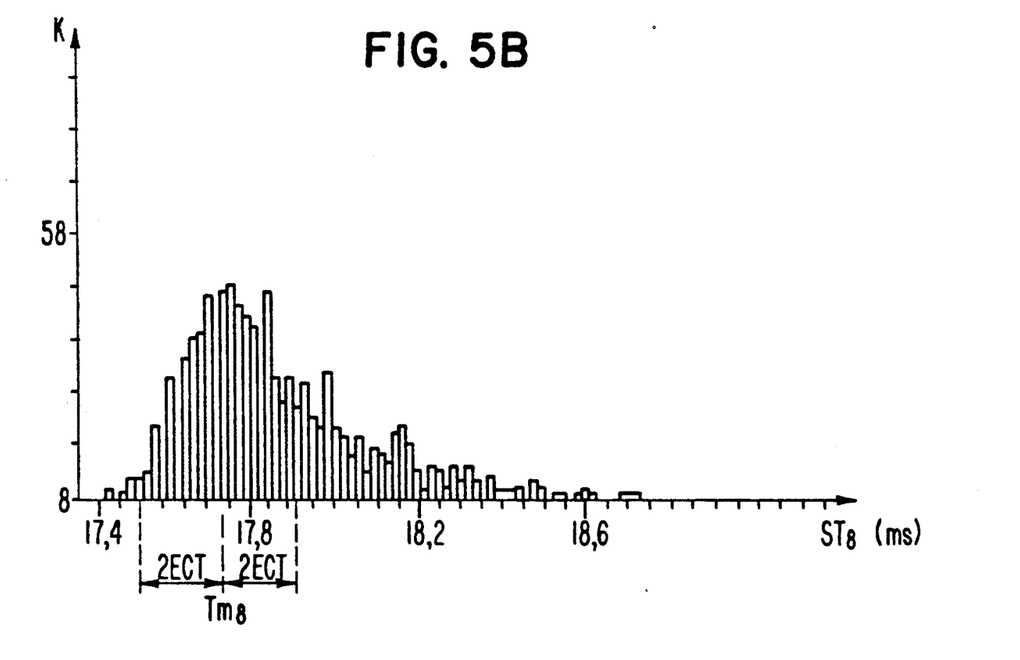

Another method may be envisaged for eliminating the effects of such an asymmetrical implantation in the case of a high frequency pulse signal. According to FIG. 3, the rotation periods are defined to correspond to the time taken by the same blade or by the same mark to complete one turn of rotation. For N=4, each rotation period is equal to the duration of 4 successive pulses. FIGS. 5A and 5B respectively show an example of the distribution of the rotation periods $ST_7(i)$ and $ST_8(i)$ determined for a given calibration stage. The rotation periods are then processed so as to determine the corresponding mean calibration periods.

A first possible method for processing the values lies in establishing the relationship between the sum of the rotation periods and the number of periods to determine the mean calibration period $Tm_7$, $Tm_8$, i.e.:

$$Tm_7 = \frac{1}{j} \cdot \sum_{i=1}^{j} ST_7(i)$$

and $$Tm_8 = \frac{1}{k} \cdot \sum_{i=1}^{k} ST_8(i)$$

Such a processing method appears particularly suitable if the rotation periods are distributed according to a Gaussian curve, as illustrated in FIG. 5A.

Another method for determining the mean calibration period proves more particularly suitable for eliminating the measurement errors which are clearly apparent in FIG. 5B. In this example, it will be found that some rotation periods have high values corresponding in particular to measurement artifacts. To eliminate such measurement errors, the mean calibration period Tm is determined, so that the maximum of the values of the rotation periods is situated in the interval I centred round this mean period Tm. Moreover, provision may be made for the mean calibration period Tm thus determined, to by validated to the extent that the number of the measured rotation periods contained in this interval I is higher than or equal to a predetermined percentage of the total number of the measured values of the rotation periods.

By way of example, the calibration will be validated if 80% of the values of the rotation periods are contained in the predetermined interval I and centred round the mean period Tm.

Preferably, the interval I is the interval comprised between the value of the mean period Tm plus twice a standard deviation (ECT) and the value of the mean period Tm less twice a standard deviation (ECT). Such a standard deviation is determined under static measurement conditions from the analysis of the data provided by the same type of flowmeter used during the calibration and dialysis stages.

The calibration process described above, whose method lies in measuring the elementary periods between two pulses allows a high measurement accuracy to be obtained and which is independent of the calibration duration. Moreover, this method allows a large number of data to be obtained permitting a suitable processing of the measurements, to eliminate accidental metering errors. It follows therefrom that the calibration duration can be limited to a minimum duration necessary for the acquisition of sufficient data for subsequent processing without, however, affecting the measurement accuracy, because the errors liable to appear during this very short space of time are eliminated by the calibration method in accordance with the invention. By way of example, practical experience has shown that the stage of calibrating the two flowmeters can be obtained during a period of the order of 10 seconds.

Figure 6:
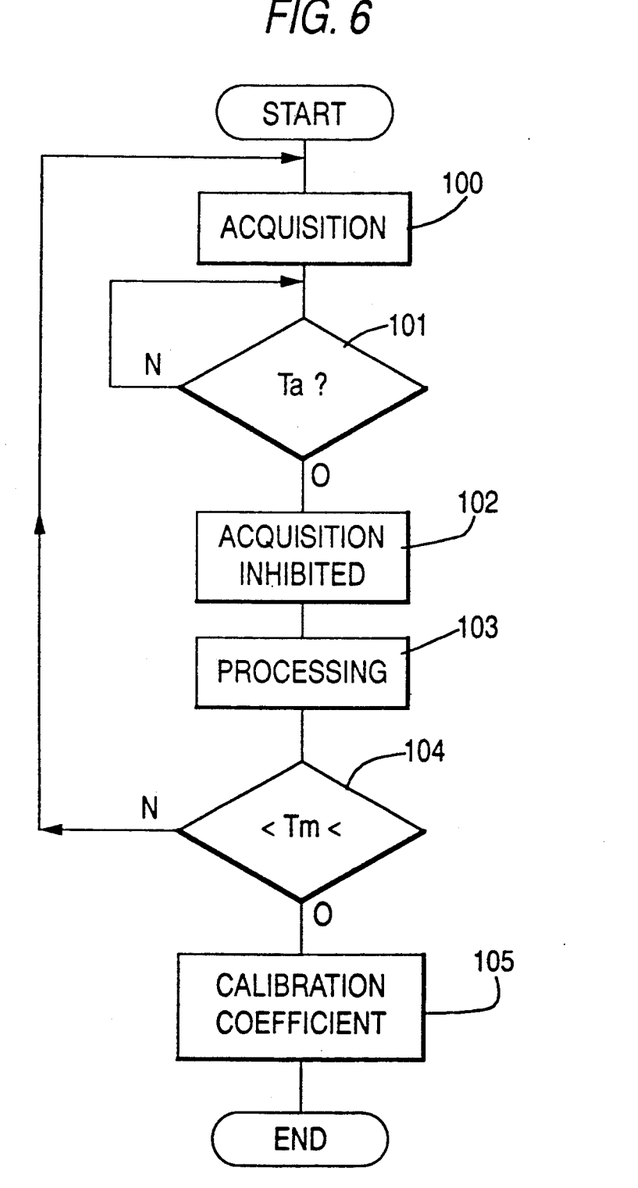
FIG. 6 illustrates a simplified algorithm describing the calibration method in accordance with the invention.

Of course, the calibration method in accordance with the invention can be advantageously operated by programming means located in a microprocessor forming an integral part of the control and processing device 11. The programming means comprise, moreover, a main calibration algorithm as illustrated in FIG. 6. This algorithm has an initialization step 100 during which the elementary periods of each one of the flowmeters are acquired, for example according to the following method. An interruption signal transmitted to the microprocessor is generated at each descending front of a pulse. The interruption signal allows a buffer stage 11a to be read, wherein the value of a counter 11b is continuously registered. At the moment of each interruption, the value of the counter contained in the buffer stage is stored and then it is subtracted from that previously registered so as to determine an elementary period. Of course, the number of interruptions is registered to ascertain the number of pulse emitted during the elementary periods.

The elementary periods are acquired while the recording time Ta of a flowmeter has not been completed (step 101).

When the elementary periods of each of the flowmeters have been successively registered, the interruption signals are inhibited (step 102) so as to permit the processing of the data taken into account according to the method described above (step 103).

If the mean calibration period calculated does not make it possible to obtain a specified percentage of rotation period values comprised in the chosen interval centred round this mean, a calibration error signal is emitted and a fresh data acquisition stage must be effected (step 104).

When the calibration periods of each flowmeter are accurately determined, the control device 11 determines a calibration coefficient which may be, for example, the ratio between the two calculated mean calibration periods (step 105). This calibration coefficient makes it possible to correct the flow measurements undertake by the flowmeters during the dialysis session.

As shown in FIG. 1, to proceed to such a dialysis session following the initial calibration stage, the means 16 is placed into its obturation position, whilst the means 15 is placed into the open position so that the dialysis liquid is circulating in the circuit A, C, D, F, by traversing in particular the compartment 2 of the haemodialyser 3. According to a preferred mode of operation, an extraction pump 17 is mounted in the dialysis circuit, for example, between the circulating pump 13 and the outlet D of the haemodialyser so as to extract from the circuit 1 a quantity of dialysis liquid equal to the quantity of ultrafiltrate to be withdrawn from the blood.

Advantageously, the flow of the dialysis liquid during the calibration stage is chosen to have the same value as the flow of the dialysis liquid circulating during the dialysis session.

Preferably, a true calibration coefficient can be determined by proceeding to the half-sum of the two coefficients defined according to two successive calibration stages. This true calibration coefficient corresponds to the one that should have been used during the dialysis stage between two consecutive calibration stages. Thus the control device 11 determines a correction coefficient corresponding to the deviation between the true coefficient and the first of the two coefficients considered, making it possible to correct by means of this coefficient, the relative volume of liquid metered by the flowmeters between the two successive calibration stages considered.

If the flow value of the dialysis liquid is modified significantly during the dialysis session, a fresh calibration stage must be effected with this new flow value of the dialysis liquid so as to determine a new calibration coefficient. Such a calibration stage can be advantageously effected according to the method of the invention, inasmuch as the calibration period is limited in time.

It is thus apparent that the method in accordance with the invention of calibrating at least one flowmeter finds a particularly advantageous application for flow meters equipping a circuit of dialysis liquid. Indeed, the method in accordance with the invention allows the flowmeters to be calibrated in a very short time, while eliminating accidental metering errors, so that the efficiency of the dialysis remains unimpaired.

The invention is not limited to the examples described and represented because various modification may be introduced into it without departing from its scope.

What is claimed is:

1. A calibration method for a flowmeter delivering an electric pulse signal whose frequency corresponds to the rate of flow of a fluid circulating in a circuit, the method including the steps of:

measuring during a data acquisition stage of a specified duration (Ta), each elementary period ($T_7(i)$, $T_8(i)$) separating two pulses staggered by a specified measurement span;

counting the number of pulses (n, m) emitted during the acquisition stage (Ta); and calculating the mean calibration period ($Tm_7$, $Tm_8$).

2. A calibration method according to claim 1, wherein the step of calculating the mean calibration period includes the substep of establishing a ratio of a sum of elementary periods to a number of counted pulses.

3. A calibration method according to claim 1, suitable for a rotary flowmeter with N pulses generated per rotor turn, wherein the step of calculating the mean calibration period includes the substeps of:

calculating successive rotation periods ($ST_7(i)$, $ST_8(i)$), by proceeding for each one of them to the summation of N consecutive elementary periods $T_7(i)$, $T_8(i)$; and processing the rotation periods for determining the mean calculation period.

4. A calibration method according to claim 3, wherein the successive rotation periods ($ST_7(i)$, $ST_8(i)$) are chosen to overlap at least one elementary period ($T_7(i)$, $T_8(i)$).

5. A calibration method according to claim 4, wherein the measurement span (P) corresponds to one pulse, and the successive rotation periods ($ST_7(i)$, $ST_8(i)$) are chosen to overlap (N−1) elementary periods ($T_7(i)$, $T_8(i)$).

6. A calibration method according to one of claims 3, 4, or 5, wherein the step of processing the rotation periods ($ST_7(i)$, $ST_8(i)$) includes the substep of establishing a ratio of the sum of the rotation periods to a number of periods, to determine a mean calibration period ($Tm_7$, $Tm_8$).

7. A calibration method according to one of claims 3, 4, or 5, wherein the step of processing the rotation periods includes the substeps of:
   determining a mean calibration period (Tm), so that a maximum of the values of the rotation periods is situated in an interval (I) centered around this mean period; and
   validating the calibration if a number of measured rotation periods contained in the interval (I) is higher than a predetermined percentage of a total number of the values of the rotation periods.

8. A calibration method according to claim 7, wherein the interval (I) lies between a value of the mean period (Tm) plus twice a standard deviation (ECT) and a value of a mean period (TM) less twice the standard deviation (ECT).

9. A calibration method according to one claims 3, 4, or 5, wherein the step of processing the rotation periods includes the substeps of:
   determining a mean calibration period (Tm), so that a maximum of the values of the rotation periods is situated in an interval (I) centered around this mean period; and
   validating the calibration if a number of measured rotation periods contained in the interval (I) is equal to a predetermined percentage of a total number of the values of the rotation periods.

10. A calibration method according to claim 3, wherein the measurement span (P) corresponds to (N) pulses.

11. A calibration method according to claim 1, wherein the measurement span (P) corresponds to one pulse.

12. A calibration method according to one of claims 1, 2, 3, 4, 5, 8, 10, or 11 involving a pair of flowmeters, one of which is mounted at an intake and the other at an outlet of a dialysis circuit, of the type constituted by proceeding to at least one calibration stage during which the rate of flow of the dialysis liquid is identical at the intake and at the outlet of the circuit, by way of bypassing the haemodialyser, wherein the step of determining the mean calibration period ($Tm_7$, $Tm_8$) includes determining a calibration period for each flowmeter, and defining a calibration coefficient corresponding to the ratio of two mean calibration periods.

13. A calibration method according to claim 12, further comprising the step of choosing during the calibration stage, a flow rate of the dialysis liquid circulating in the circuit having the same value as a normal circulation flow rate during an operating stage of the haemodialyser.

14. A calibration method according to claims 11, further comprising the step of proceeding, during an operating stage of the haemodialyser, to calibration stages staggered in time, in order to determine successive calibration coefficients.

15. A calibration method according to claim 14, further comprising the steps of:
   defining a true calibration coefficient determined by a half-sum of two coefficients defined according to two successive calibration; and
   correcting a relative volume of liquid metered between two successive calibration stages by a correction coefficient corresponding to a deviation between the true coefficient and the first coefficient of the two coefficients considered.

16. A control and processing unit for calibrating a system of two flowmeters, each flowmeter delivering an electric pulse signal (S) whose frequency corresponds to a rate of flow of a fluid, the unit comprising:
   a microprocessor connected to the flowmeters for receiving information corresponding to elementary periods ($T_7(i)$, $T_8(i)$) separating two pulses staggered by a specified measurement span (P);
   a counter for measuring each elementary period separating two pulses emitted by each one of the flowmeters;
   means for counting the pulses emitted during considered elementary periods; and
   programming means for processing the elementary periods to determine a mean calibration period for each flowmeter.

17. A calibration device for a flowmeter which delivers an electric pulse signal (S) whose frequency corresponds to the rate of flow of a fluid, the device comprising:
   means for measuring during a data acquisition state of a specified duration (Ta), elementary periods ($T_7(i)$, $T_8(i)$) separating two pulses staggered by a specified measurement span (P);
   means for counting a number of pulses (n, m) emitted during the data acquisition stage (Ta); and
   means for calculating an average calibration period ($Tm_7$, $Tm_8$).

* * * * *

UNITED STATES PATENT AND TRADEMARK OFFICE
CERTIFICATE OF CORRECTION

PATENT NO. : 5,111,683

DATED : May 12, 1992

INVENTOR(S) : Andre FOND

It is certified that error appears in the above-identified patent and that said Letters Patent is hereby corrected as shown below:

Claim 1, col. 8, line 52, after "span" insert --(P)--.

Claim 14, col. 10, line 13, change "claims 11" to --claim 12--.

Claim 15, col. 10, line 22, after "calibration" insert --stages--.

Signed and Sealed this

Twenty-ninth Day of June, 1993

Attest:

MICHAEL K. KIRK

*Attesting Officer*  Acting Commissioner of Patents and Trademarks